(12) United States Patent
Jungo (10) Patent No.: US 11,549,966 B2
(45) Date of Patent: Jan. 10, 2023

(54) INTERFACE UNIT FOR COUPLING A PROBE TO A MEASURING SYSTEM

(71) Applicant: Mettler-Toledo GmbH, Greifensee (CH)

(72) Inventor: Daniel Jungo, Geroldswil (CH)

(73) Assignee: METTLER-TOLEDO GMBH, Greifensee (CH)

(*) Notice: Subject to any disclaimer, the term of this patent is extended or adjusted under 35 U.S.C. 154(b) by 321 days.

(21) Appl. No.: 17/011,430

(22) Filed: Sep. 3, 2020

(65) Prior Publication Data

US 2021/0072285 A1 Mar. 11, 2021

(30) Foreign Application Priority Data

Sep. 10, 2019 (EP) ..................................... 19196402

(51) Int. Cl.
*G01R 1/067* (2006.01)
*G01N 27/416* (2006.01)
*G01N 33/00* (2006.01)

(52) U.S. Cl.
CPC ..... *G01R 1/06766* (2013.01); *G01N 27/4167* (2013.01); *G01N 33/004* (2013.01); *G01N 33/0039* (2013.01)

(58) Field of Classification Search
CPC ........... G01R 1/06766; G01N 27/4167; G01N 33/0039; G01N 33/004
See application file for complete search history.

(56) References Cited

U.S. PATENT DOCUMENTS

| | | | |
|---|---|---|---|
| 3,855,101 A * | 12/1974 | Wilson | G01N 27/48 327/28 |
| 4,521,741 A | 6/1985 | Ruberl | |
| 5,914,545 A * | 6/1999 | Pollersbeck | H03K 17/0822 307/131 |
| 6,353,323 B1 | 3/2002 | Fuggle | |
| 7,177,127 B2 | 2/2007 | Hamilton et al. | |
| 2015/0212041 A1 | 7/2015 | Stahl | |

FOREIGN PATENT DOCUMENTS

| | | |
|---|---|---|
| EP | 0922955 A2 | 6/1999 |
| EP | 2861975 B1 | 11/2016 |

OTHER PUBLICATIONS

Extended European Search Report dated Feb. 24, 2020, issued by the European Patent Office in the corresponding European Patent Application No. 19196402.2-1020. (5 pages).
Ryan Edwards: "Ion Selective Electrode Interface—Sparky's Widgets", Apr. 21, 2017, as retrieved from the Internet URL https://www.sparkyswidgets.com/portfolio-item/ion-selective-electrode-interface/ on Apr. 2018.

* cited by examiner

*Primary Examiner* — Andrew Schechter
*Assistant Examiner* — James M Bui
(74) *Attorney, Agent, or Firm* — Buchanan Ingersoll & Rooney PC (57) ABSTRACT

The present disclosure relates an interface unit having an input for receiving an input voltage from an electrochemical measuring probe; a first transistor; a first operational amplifier; a second transistor; and a second operational amplifier. The first operational amplifier is arranged to provide a variable tension to a first source terminal of the first transistor, in accordance with a comparison between a reference voltage and a second resistor voltage, in order to control an operating point of the first transistor.

18 Claims, 4 Drawing Sheets

INTERFACE UNIT FOR COUPLING A PROBE TO A MEASURING SYSTEM

RELATED APPLICATION

This application claims priority under 35 U.S.C. § 119 to European Patent Application No. 19196402.2 filed in Europe on Sep. 10, 2020, the entire content of which is hereby incorporated by reference in its entirety.

FIELD

The present disclosure relates to an interface unit for coupling the output on which a measuring probe delivers a voltage generated by an electrode, to an input of a measuring system for processing the voltage signal into measurements related to at least one property of a process material when the electrode is in contact with the process material.

The interface unit and the corresponding method allows coupling, to a measuring system, measuring probes, such as for example an ion-sensitive measuring probe, in particular a pH measuring probe, an oxygen measuring probe, a $CO_2$ measuring probe, or an ozone measuring probe.

BACKGROUND INFORMATION

The monitoring and control of industrial processes, for example in the chemical and pharmaceutical industries, in the textile industry, in the food and beverage industries, in the processing of paper and cellulose, or in the fields of water processing and waste water treatment, is based on the measurement of process variables that are determined by means of suitable measuring probes.

According to "Process Measurement Solutions Catalog 2005/06", Mettler-Toledo GmbH, CH-8902 Urdorf, Switzerland, pages 8 and 9, a complete measuring system contains (e.g., consists of) a housing, a measuring probe, a cable and a measurement converter (also called a transmitter). By means of the housing, the measuring probe is brought into contact with the process that is to be measured or monitored, for example by immersing the probe in the process material and holding it there. The measuring probe serves to measure specific properties of the process. Measurement signals are sent through the cable to the transmitter, which communicates with a process control system and converts the measuring signals into readable data. The measuring probes are selected depending on the process material properties that are to be measured.

There are numerous situations in which the measuring probe can be exposed to high temperature, commonly 140° C. (degree Celsius) and above. For example, in a pharmaceutical, medical or industrial food production context, the measuring probe may be in contact with materials or products that should not be contaminated by infectious agents. Consequently, it is often necessary to sterilize the measuring probe using an autoclave. In an exemplary use case, during its entire life span, a measuring probe goes through the autoclaving process between 30 and up to 100 times. Measuring probes, such as ion-sensitive measuring probes, are known to carry a current through their sensing element, which is inherent to their functional principle. The higher the temperature, the lower the resistance of the sensing element. For example, the glass resistance of the sensing element in a pH measuring probe decreases drastically as the temperature reaches and exceeds 100 degree Celsius.

In order to amplify the voltage of the measuring signal to a suitable level, it is known to couple the output of the sensing element of the measuring probe to an input stage circuit provided with an operational amplifier. Such solutions are disclosed for example in U.S. Pat. No. 7,177,127 B2, EP 2861975 B, EP 0 922 955 A2 or Ryan Edwards: "Ion Selective Electrode Interface—Sparky's Widgets", 21 Apr. 2017, as retrieved from the Internet URL https://www.sparkyswidgets.com/portfolio-item/ion-selective-electrode-interface/ on April 2018. Under normal operations, when the input stage circuit is switched on, the impedance of the input stage circuit is at a high level. By contrast, when the input stage circuit is switched off and/or is in an unpowered state, the impedance of the input stage circuit falls to a low level, for example, less than 1 kOhm (k$\Omega$). When the input stage circuit is switched to zero current flow, which is often done during a high temperature process, the residual current rises between the sensing element and the input stage circuit, due to the low impedance of the operational amplifier, the input stage being in unpowered state. The current flowing through the sensor element increases drastically and may reach hazardous levels, causing very slow signal drifts and lasting damages to the sensor element.

At high temperatures above 100 degree Celsius, this issue is compounded by the sensible decrease of isolating characteristics of the semiconductors used in the operational amplifier for electrostatic discharge protection. In this context, the electrostatic discharge protection diode found in the operational amplifier may even cause short circuits.

These issues are even more critical for sensing elements that are provided with an active voltage source, such as a solid-state pH sensor.

A partial solution to connect an active sensing element to an input stage circuit of a measuring system while mitigating the above-mentioned current leakage issues, are known from EP 1 010 249 B1. However, these kinds of input stages do not allow connection of a probe delivering a sensing voltage varying according to a wide range of values, known to be between 0.25 and 5.5 Volt, without introducing significant saturation and/or distortion issues into the output signal. Moreover, the known input stages are subject to electronic component manufacturing variation, introducing measurement errors.

Thus, there is a need for an improved interface unit for coupling the output voltage of a sensor element of a measuring probe, for example a potentiometric measuring probe such as an ion-sensitive measuring probe, to the input of the measuring system for processing the output voltage into measurements, the output voltage of the sensor element varying over a wide range of values, for example, between 0.25and 5.5 Volt, and in which current flowing through the sensor element is particularly low, for example, lower than 1 pA, in particular when temperature reaches a high level, for example, from 100 degree Celsius, and/or when the input stage circuit is in an unpowered off state, especially if the sensing element is provided with an active voltage source, such as a solid-state pH sensor, while preserving the accuracy of the measurements affected negatively by the combination of high temperature and the lower impedance of the input stage circuit.

The entire contents of the documents mentioned herein are incorporated by reference in their entireties.

SUMMARY

An interface unit is disclosed, comprising: an input configured and adapted to receive an input current having an input voltage ($V_{IN}$), from an electrochemical measuring probe for use in contact with a process material, the electrochemical measuring probe having an electrode (EL) provided with a sensing element arranged so as to generate a sensor voltage ($V_{SENSOR}$) as an electrode voltage related to at least one property of the process material when the electrode is in contact with the process material; an output configured and adapted to be coupled to an input of an evaluating device, the interface unit being configured to deliver, on the output, an output current having an output voltage ($V_{OUT}$) essentially equal to the input voltage ($V_{IN}$); a first transistor provided with a first insulated gate terminal coupled to the input, a first source terminal coupled to a first terminal of a first resistor, and a first drain terminal coupled to a first terminal of a second resistor, a second terminal of the second resistor being coupled to a point where a constant voltage ($V_C$) is maintained to a constant value, the first transistor being configured and arranged to generate in the second resistor a second resistor voltage ($V_{R2}$), according to the input voltage ($V_{IN}$); a first operational amplifier provided with a first non-inverting input coupled to a circuit point where a reference voltage ($V_{ref}$) is maintained to a constant value, with a first inverting input coupled to a first drain terminal of the first transistor, and with a first output coupled to a second terminal of the first resistor; a second transistor provided with a second source terminal coupled to a second terminal of a third resistor, and a second drain terminal coupled to a first terminal of a fourth resistor, a first terminal of the third resistor being coupled to the second terminal of the first resistor, a second terminal of the fourth resistor being coupled to a point where the constant voltage ($V_C$) is maintained; and a second operational amplifier provided with a second non-inverting input coupled to the second drain terminal of the second transistor, and with a second inverting input coupled to the first inverting input of the first operational amplifier, and with a second output coupled a second insulated gate terminal of the second transistor and to the output of the interface unit; wherein the first operational amplifier is configured and arranged to provide a variable tension to the first source terminal of the first transistor in accordance with a comparison between the reference voltage ($V_{ref}$) and the second resistor voltage ($V_{R2}$), in order to control an operating point of the first transistor.

BRIEF DESCRIPTION OF THE DRAWINGS

Details of exemplary embodiments of the disclosed method and device will become apparent from the detailed description of the exemplary embodiments which are shown in schematic and simplified representation in the drawings, wherein.

DETAILED DESCRIPTION

To that end, according to a first aspect, exemplary embodiments of the present disclosure concern an interface unit including an input configured and adapted to receive an input current having an input voltage, from an electrochemical measuring probe for use in contact with a process material.

The electrochemical measuring probe includes an electrode provided with a sensing element arranged so as to generate a sensor voltage. The electrode voltage is related to at least one property of the process material when the electrode is in contact with the process material.

The electrochemical measuring probe is for example a potentiometric measuring probe. More particularly, the electrochemical measuring probe may be selected from the non-exhaustive group consisting of, for example: a pH measuring probe, an oxygen measuring probe, a $CO_2$ measuring probe, and an ozone measuring probe.

In known operational conditions, according to the temperature, the impedance of the sensing element is for example between approximately (i.e., ca., +/−10%) 500 MOhm and ca. 20 GOhm.

The sensing element of the electrode can include an active layer behaving as a voltage source, the electrode voltage differing from zero even when the electrode is not in contact with the process material.

For example, the electrode can include a solid-state pH sensor having an active layer behaving as a voltage source. The electrode can include an ion pH-sensitive glass substrate and several layers on top of the ion pH-sensitive glass substrate. The layers can include a base (e.g., elementar) lithium layer, a lithium phosphorus oxynitride (generally designated by the acronym LiPON) layer, and a protective layer configured and adapted to limit degradations of the lithium layer as well as to provide a packaging structure for stabilizing the whole glass electrode against environmental factors. The electrical potential of the glass electrode of the measuring probe differs from zero (is not null), even when the glass electrode is not in contact with the process material.

The interface unit can include an output configured and adapted to be coupled to the input of an evaluating device. For example, the evaluating device serves as measurement converters, and is coupled to a processing device, for example a computer. In known operational conditions, the input impedance of the evaluating device is low, for example between ca. 100 kOhm and ca. 10 MOhm.

The interface unit is arranged to deliver, on the output, an output current having an output voltage essentially equal to the input voltage. For example, an offset voltage between the input voltage and the output voltage of the interface unit may be lower or equal to +/−10 mV. The offset voltage remains essentially constant under the normal range of temperatures reached at the sensor coupled to the interface unit, for example, from ca. 0° C. to ca. 100° C., regardless of the input voltage.

In an advantageous exemplary embodiment, the electrical specifications of the electrical components of the interface unit, and more particularly the tolerances of the electrical components, such as the tolerance of the nominal values of the resistors are set so that the tolerance for the difference between the output voltage of the interface unit and the input voltage is at least equal or less than +/−0.1%. Accordingly, the offset voltage between the input voltage and the output voltage of the interface unit may be lower or equal to +/−2 mV. The offset voltage remains essentially constant under the normal range of temperatures reached at the sensor coupled to the interface unit, for example, from ca. 0° C. to ca. 100° C., regardless of the input voltage.

Advantageously, the interface unit can include means for adjusting the output voltage by compensating for the offset voltage. Since the offset voltage remains essentially constant under the normal range of temperatures reached at the sensor coupled to the interface unit and regardless of the input voltage, a calibration step may be carried out once and stored in the interface unit. More particularly, the interface unit may be calibrated, after having been assembled. To that end, precisely measured and stable calibration signals may be applied as input voltage signals of the interface unit. The resulting output voltages of the interface unit are then measured: gain and offset values are then computed in order to compensate for discrepancies between the calibration signals and the output voltages, and may be stored in the interface unit, for example in an EEPROM controller. The gain and offset values may be accessed on demand, for example by a measuring software in order to compensate measurements values.

The interfacing unit can include a first transistor provided with a first insulated gate terminal coupled to the input, a first source terminal coupled to a first terminal of a first resistor, and a first drain terminal coupled to a first terminal of a second resistor. The second terminal of the second resistor can be coupled to a point where a constant voltage is maintained to a constant value; the first transistor can be arranged to generate in the second resistor a second resistor voltage, according to the input voltage.

The interfacing unit can include a first operational amplifier provided with a first non-inverting input coupled to a point of the circuit where a reference voltage is maintained to a constant value. The exemplary first operational amplifier is also provided with a first inverting input coupled to the first drain terminal of the first transistor. The first operational amplifier is also provided with a first output coupled to a second terminal of the first resistor.

The interfacing unit can include a second transistor provided with a second source terminal coupled to a second terminal of a third resistor, and a second drain terminal coupled to a first terminal of a fourth resistor. The first terminal of the third resistor is coupled to the second terminal of the first resistor. The second terminal of the fourth resistor is coupled to a point where the constant voltage is maintained.

The interfacing unit can include a second operational amplifier provided with a second non-inverting input coupled to the second drain terminal of the second transistor. The exemplary second operational amplifier is also provided with a second inverting input coupled to the first inverting input of the first operational amplifier. The second operational amplifier is also provided with a second output coupled a second insulated gate terminal of the second transistor and to the output of the interface unit.

The first operational amplifier is arranged to provide a variable tension to the first source terminal of the first transistor, according to a comparison between the reference voltage and the second resistor voltage, in order to control the operating point of the first transistor.

The interface unit can act as an impedance buffer for transmitting a weak input signal received from a high impedance input to a low impedance output.

According to exemplary embodiments of the present disclosure, the evaluating device is not directly fed by the electrode voltage itself nor an amplified voltage obtained directly by pre-amplifying the electrode voltage, as is known to be done in conventional input stage circuits, but by the decoupled voltage delivered by the interface unit. Moreover, the electrode voltage is fed in the input through the first transistor through its insulated gate, providing a high insulation barrier. The interface unit provides an efficient current barrier, avoiding any significant load to be flowing through the input, and for example, less than 1 pA. Consequently, the sensor element of the electrode is not charged anymore, thanks to the decoupling effect of the interface unit. Even at high temperatures, for example during an autoclaving process, the residual current on the sensor element of the electrode EL can be kept exceptionally low. It provides an efficient solution to limit considerably negative effects on the electrode of residual currents, in particular when the measuring probe is switched to zero current flow, which is often done during a high temperature process.

By using transistors provided with an insulated gates, an exemplary embodiment of interface unit according to the present disclosure allows coupling output signal-processing units having a known (e.g., conventional) input stage circuit, including an operational amplifier.

Moreover, since the influence of residual current on the sensor element of the electrode EL is drastically reduced by the action of the transistor with the insulated gate, the interface unit according to exemplary embodiments of the present disclosure allows use of an electrode having an active layer behaving as a voltage source, even in environments where temperature reaches and exceeds 100 degree Celsius. For electrodes with sensor elements including an elementar lithium layer, it allows for drastic (e.g., significant) reduction in consumption of elementar lithium, and can improve the life span of the probe. This is for example advantageous for solid-state pH sensors.

The first operational amplifier is arranged to control the operating point, also known as Q-point or bias point, of the first transistor so as that the first transistor operates without saturation, distortion or other non-linear disturbances, for a wide range of values of the input voltage, for example, between 0.25 and 5.5 Volt. The first operational amplifier remains at almost the same operating point, over a wide range of values of the input voltage. Moreover, since the gate of the first transistor is not linearly controlled in relation with the current flowing between the source and the drain of the first operational amplifier, maintaining a fixed operating point allows increased accuracy of the behavior of the first operational amplifier, by reducing non-linear behavior over a wide range of values for the input voltage $V_{IN}$. The error introduced by the interface unit in the output voltage comparatively to the input voltage $V_{IN}$ can be drastically reduced.

By contrast, in known solutions where a steady-state DC voltage or constant current is applied for biasing the source of the transistor, the input voltage may vary only on a much more limited range of values for the input voltage compared to exemplary embodiments disclosed herein, since saturation and/or distortion issues occur due to the fixed nature of the biasing current.

Moreover, by coupling the inverting input of the second operational amplifier to the inverting input of the first operational amplifier, the interface unit is arranged to compensate for discrepancies between electronic components, due to manufacturing tolerances for instance, by adapting the output voltage of the second operational amplifier accordingly.

Advantageously, the first resistor may have a resistance essentially identical to the resistance of the third resistor; and, the second resistor may have a resistance essentially identical to the resistance of the fourth resistor. The first transistor and the second transistor may also be of the same type.

In particular, the same type of electronic component may be used for the first resistor and the third resistor. The same type of electronic component may be used for the first transistor and the second transistor. The same type of electronic component may be used for the first operational amplifier and the second operational amplifier. The interface unit then presents a balanced symmetrical design, providing an advantageous solution for reducing the cumulative influences on the interface unit of the variations of the environmental parameters, such as the variation of temperatures, of the manufacturing tolerances for the electrical components, and of the electrical noises, compared to circuits with a non-symmetrical design.

Advantageously, the first operational amplifier and the second operational amplifier may be embedded in one package of a single electronic component. The first transistor and the second transistor may also be embedded in one package of a single electronic component. These features allow to further improve the reduction of the influence of the variations of the environmental parameters, of the manufacturing tolerances for the electrical components, and of the electrical noises. Moreover, the footprint of the interface unit may be further reduced, while the production cost may be lowered.

For example, the first transistor and/or the second transistor may be chosen amongst the following exemplary list of types of transistors:
an insulated gate field-effect transistor (IGFET), without electrostatic-discharge protecting element at gate; or
a metal-oxide-semiconductor field-effect transistor (MOSFET), providing a particularly efficient insulation barrier on the gate, and being configured and adapted to be used under environments where temperature may vary broadly, and exceeds 100 degree Celsius, since an oxide layer is used between the gate and the channel of the MOSFET, to prevent current from flowing within a wide temperature range; or,
a metal-insulator-semiconductor field-effect transistor (MISFET); or
an insulated-gate bipolar transistor (IGBT).

The signal-processing unit can include an operational amplifier provided with an electrostatic discharge protection and configured so as to receive the decoupled voltage. As a consequence, it is possible to use a known input stage circuit, having standard electrostatic discharge protection, and then, use proven reliable signal-processing unit, without requiring any costly re-engineering and/or tailored made solutions.

According to a second aspect, exemplary embodiments of the present disclosure can include a measuring system having:
an interface unit according to the first aspect; and,
an electrochemical measuring probe for use in contact with a process material, including an electrode provided with a sensing element arranged so as to generate a sensor voltage, the electrode voltage being related to at least one property of the process material when the electrode is in contact with the process material; the electrochemical measuring probe being configured and adapted to deliver the sensor voltage to the input of the interface unit;
an evaluating device provided with an input configured and adapted to be coupled to the output of the interface unit, for receiving the output voltage, for converting the output voltage into measurements.

The sensing element of the electrode can include an active layer behaving as a voltage source, the electrode voltage differing from zero even when the electrode is not in contact with the process material.

The measuring probe may be selected from the exemplary group including (e.g., consisting of): a pH measuring probe, an oxygen measuring probe, a $CO_2$ measuring probe, and an ozone measuring probe.

The sensing element of the electrode can include a lithium phosphorus oxynitride layer.

Figure 1:
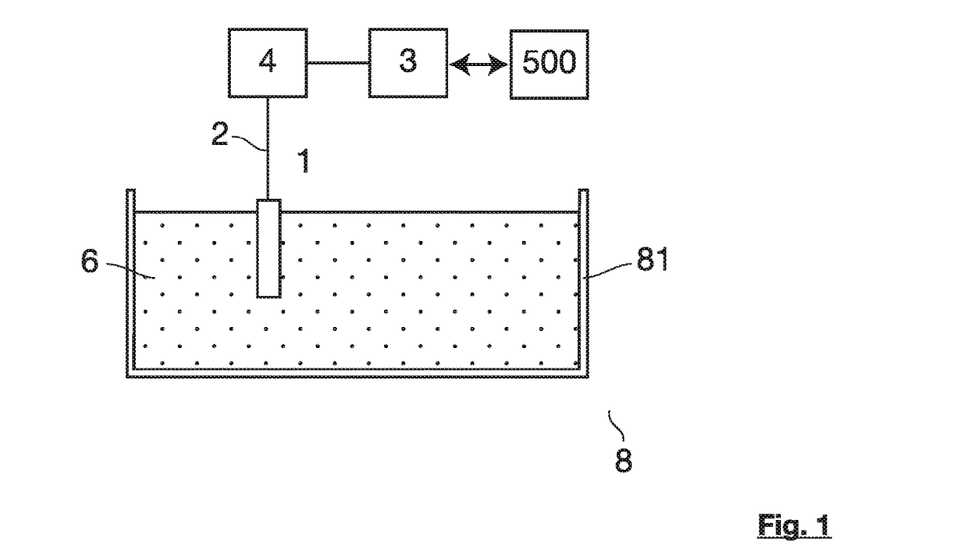
FIG. 1 illustrates a principal structure of an exemplary system for measuring at least one property of a process material 6 by a measuring probe 1.

FIG. 1 illustrates a measuring system with a container 8 including a holding vessel 81 filled with a process material 6. The properties of the process material 6 are measured by means of at least one electrochemical measuring probe 1 which is connected, through signal-transmitting device 2 to an interface unit 4. The interface unit 4 is also coupled to an evaluating device 3. The evaluating device or devices 3, which, among other functions, serve as measurement converters, is coupled to a processing device 500, for example a computer. The electrochemical measuring probe is for example a potentiometric measuring probe. More particularly, the electrochemical measuring probe may be selected from the non-exhaustive group including (e.g., consisting of): a pH measuring probe, an oxygen measuring probe, a $CO_2$ measuring probe, and an ozone measuring probe.

Figure 2:
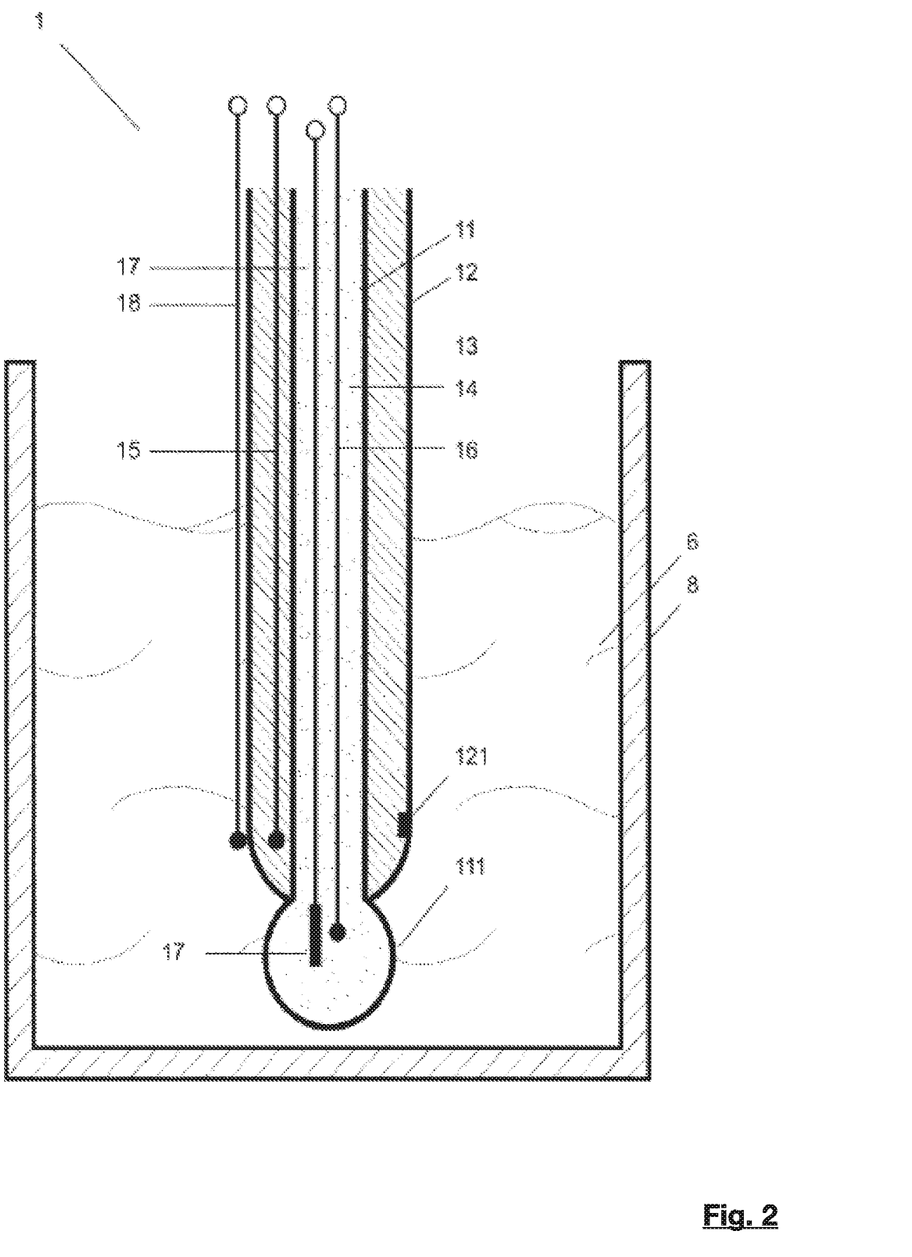
FIG. 2 schematically illustrates an exemplary electrochemical measuring probe 1, which is immersed in a process material 6 and coupled to an evaluating device 3.

The principal design structure of an electrochemical measuring probe such as for example a pH measuring probe, which in the configuration of a single rod measuring chain includes a glass electrode 16, a reference electrode 15, and an auxiliary electrode 18, is represented schematically in FIG. 2. However, exemplary embodiments are not limited to a pH measuring probe, and are also applicable to any type of electrochemical measuring probe, such as an oxygen measuring probe, a $CO_2$ measuring probe or an ozone measuring probe.

In the measuring probe 1, the glass electrode with a conductor lead element 16 and the reference electrode with a reference lead element 15 are constructively combined in one unit. Inside a first chamber within an inner tube 11 and a thin-walled glass hemisphere or glass membrane 111 adjoining the tube, the conductor lead element 16 is immersed in a solution with a defined pH value, specifically an inner buffer 14, which establishes the electrically conductive connection between the inside of the glass membrane 111 and the conductor lead element 16. Inside an outer tube 12, the reference lead element 15 is immersed in an electrolyte, specifically an outer buffer 13 which, by way of a porous separating wall or diaphragm 121, allows an exchange of electrical charges to take place with the measurement material 6.

The electrical potential at the conductor lead element 16, at the reference lead element 15, and/or at the auxiliary electrode 18 are intended to be measured and then further processed by the evaluating device 3 and the processing device 500.

In the inner buffer space, a temperature measuring sensor 17 is arranged, which provides the possibility to automatically compensate for temperature effects and to register temperature cycles.

The measuring probe 1 can include an active layer behaving as a voltage source. For example, the measuring probe 1 may be a solid-state pH sensor, the glass electrode 16 of the measuring probe 1 including for example, an ion pH-sensitive glass substrate and several layers on top of the ion pH-sensitive glass substrate. The layers can include a base (e.g., elementar) lithium layer, a lithium phosphorus oxynitride (generally designated by the acronym LiPON) layer, and a protective layer configured and adapted to limit degradations of the lithium layer as well as to provide a packaging structure for stabilizing the whole glass electrode against environmental influences. The electrical potential of the glass electrode 16 of the measuring probe 1 differs from zero (is not null), even when the conductor lead element 16 is not immersed in the holding vessel 81 filled with the process material 6. This behavior is notably due to the electrical characteristics of the elementar lithium layer and the lithium phosphorus oxynitride layer.

Figure 3:
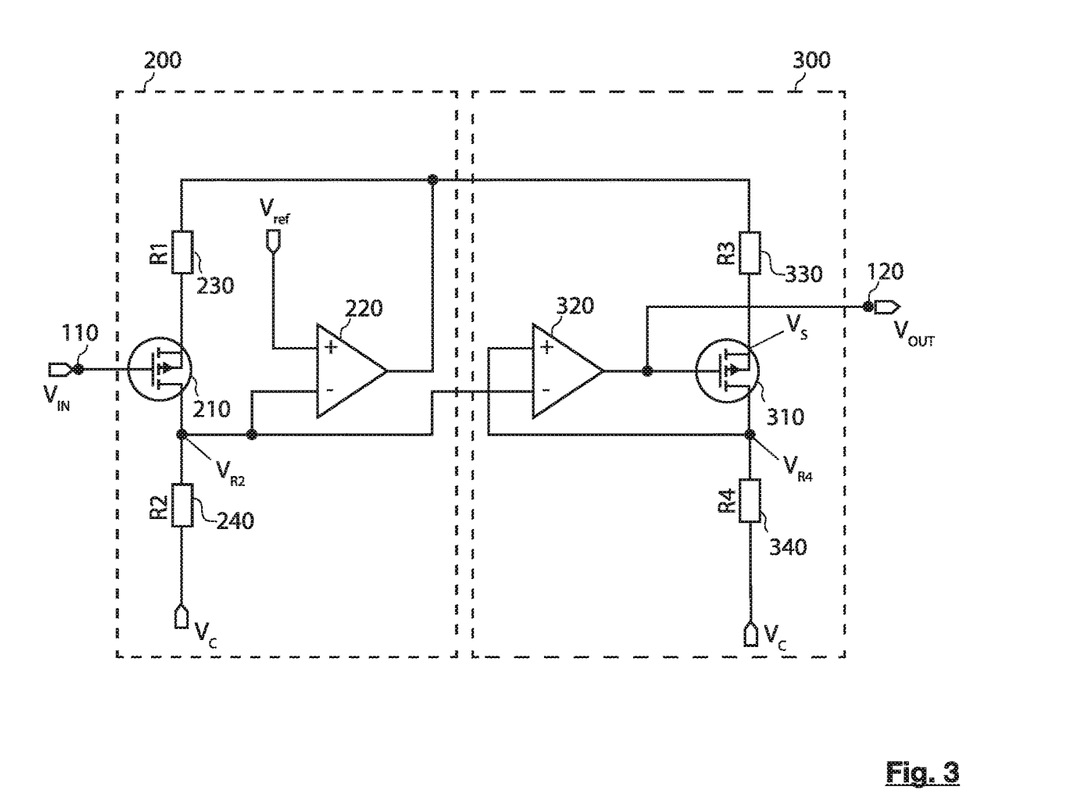
FIG. 3 represents an exemplary schematic circuit diagram of the exemplary interface unit 4.
Figure 4:
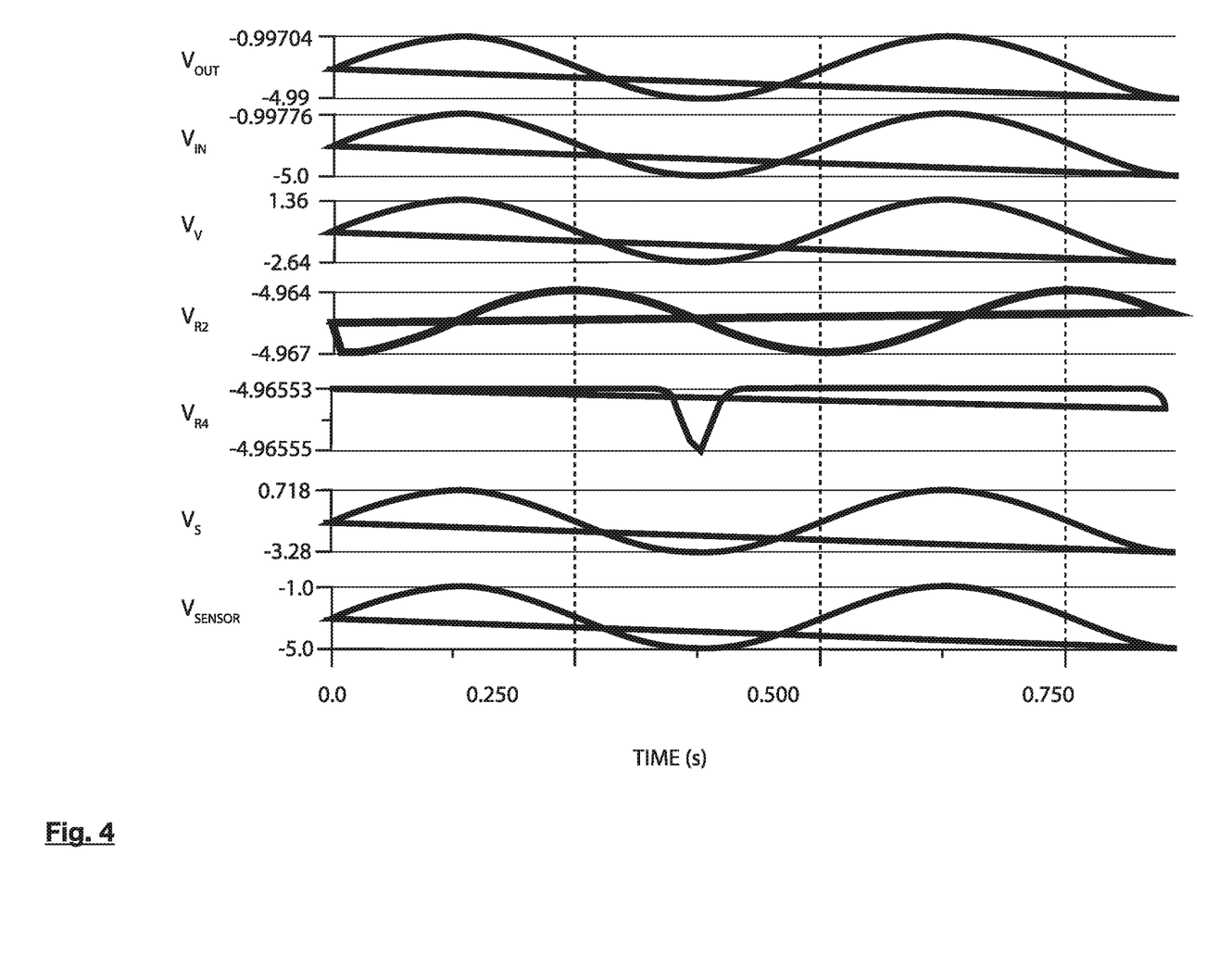
FIG. 4 represents exemplary timing diagrams of various voltages measured in the circuit of the interface unit 4, for an exemplary input voltage signal.

FIG. 3 shows a circuit diagram of the interface unit 4 in an advantageous embodiment. FIG. 4 represents, for an exemplary input voltage signal, timing diagrams of various voltages, referenced hereafter in the description, measured in the circuit of the interface unit 4. The interface unit 4 includes an input 110 configured and adapted to receive an input voltage $V_{IN}$. The input 110 is for example, configured and adapted to be coupled to an output of the measuring probe 1 which includes at least one electrode EL, for example a glass electrode and a reference electrode, so as to receive a sensor voltage $V_{SENSOR}$. Depending on the type of the measuring probe 1 used, the sensor voltage $V_{SENSOR}$ may be observed either only when the measuring probe 1 is immersed in the process material 6 or constantly, in the case of use of a solid-state pH sensor, for example. The electrode EL itself forms a voltage source SQ. When the glass electrode 16 of the measuring probe 1 is coupled to the input 110, the input impedance $Z_{in}$ observed at the input 110 is particularly high, and can be larger than 2 GOhm, under exemplary operating temperatures of the sensor, such as from ca. 0° C. to ca. 100° C. depending on the application. For instance, when the temperature of the sensor is around 25° C., the input impedance In observed at the input 110 is for example, around 2.5 GOhm. However, since the electrode resistance $R_E$ depends on the temperature observed at the measuring probe 1, the electrode resistance $R_E$ may become very small, such as, for example, lower than 50 MOhm, above 100 degree Celsius. When the measuring probe 1 includes an active layer, the sensor voltage $V_{SENSOR}$ of source SQ differs from zero, even when the conductor lead element 16 is not immersed in the holding vessel 81, for example, the voltage observed at the glass electrode 16 is around −3V when the glass electrode is not in contact with the process material 6.

Alternatively, the input 110 is for example, electrically coupled to a test or calibration devices delivering a test signal. The interface unit 4 includes an output 120 configured and adapted notably to be electrically coupled to the input of the evaluating device 2. The interface unit 4 is configured to deliver on the output 120 an output voltage $V_{OUT}$. When the input of the evaluating device 2 is coupled to the output 120, the output impedance $Z_{OUT}$ observed at the output 120 is particularly low, and, for example, lower than 100 Ohm.

Figure 5:
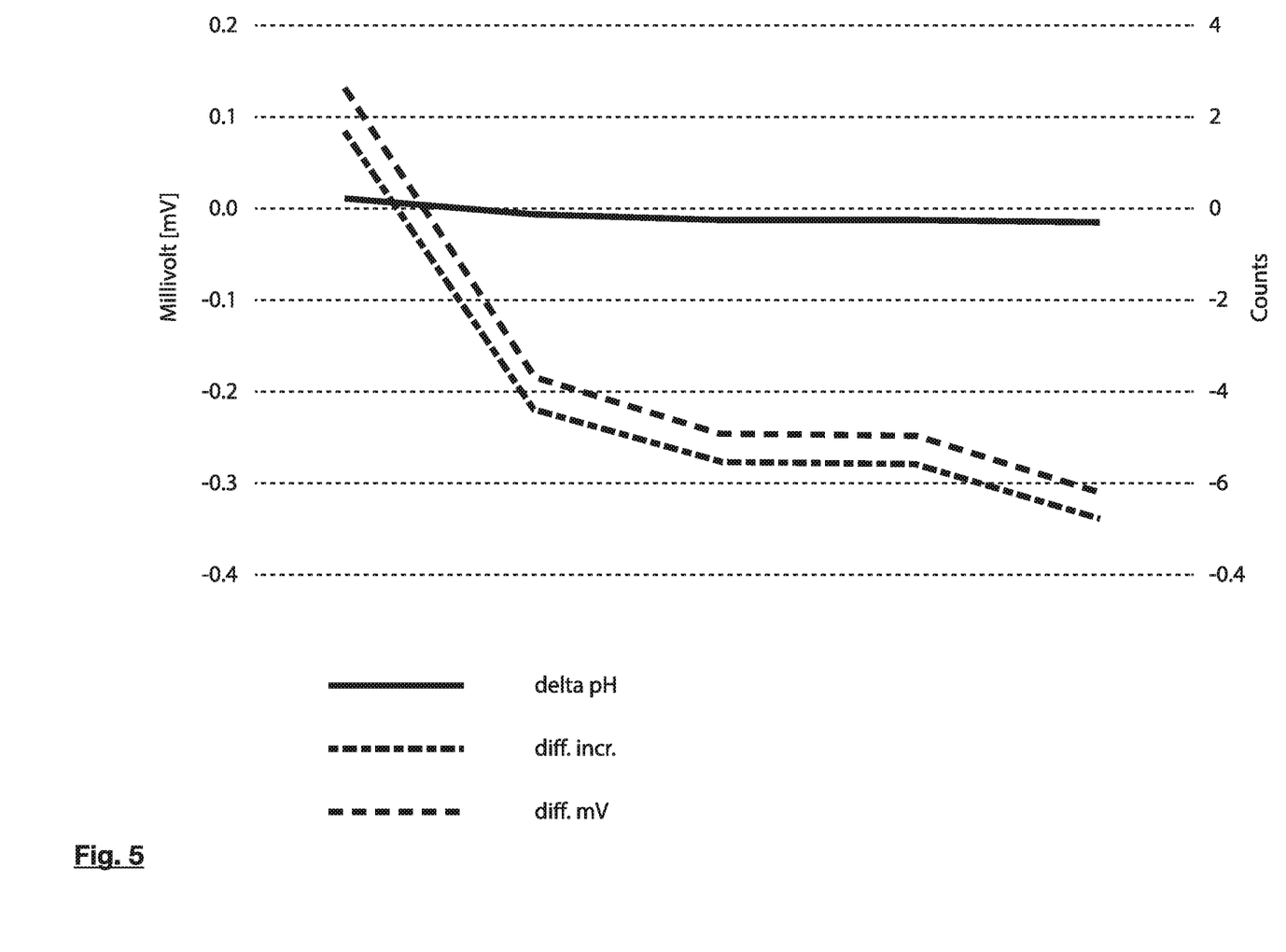
FIG. 5 represents an exemplary error diagram where an offset voltage differential (mV) between the input voltage and the output voltage of the interface unit and the related measurement errors are represented over time (abscissa representing time in milliseconds).

The interface unit 4 is arranged so as that the input voltage $V_{IN}$ observed at the input 110 is mirrored in the output 120, that is to say that, over time, the output voltage $V_{OUT}$ is maintained essentially equal to the input voltage $V_{IN}$. For example, as illustrated in FIG. 5, the difference between the input voltage and the output voltage can, for example, be between 0.1 mV and −0.4 mV for an input voltage varying from 0.25 V to 5.5 V.

The interface unit 4 is also acting as an impedance buffer for transmitting a weak input signal received from a high impedance input to a low impedance output. The interface unit 4 is also providing a current barrier, avoiding any significant load to be flowing through the input 110, and for example, less than 0.2 pA. Consequently, the sensor element of the electrode EL is not charged anymore, due to the interface unit 4. As such, even at high temperatures, for example during an autoclaving process, the influence of residual current on the sensor element of the electrode EL can be kept exceptionally low. It provides an efficient solution to limit considerably negative effects on the electrode EL of residual currents, such as when the measuring probe 1 is switched to zero current flow, which is often done during a high temperature process.

The exemplary interface unit 4 further is provided with a decoupling circuit 200 and a potential mirroring circuit 300.

The decoupling circuit 200 includes a first transistor 210, a first operational amplifier 220, a first resistor 230 presenting a resistance R1 and a second resistor 240 presenting a resistance R2. The first transistor 210 is provided with an insulated gate terminal coupled to the input 110.

The potential mirroring circuit 300 includes a second transistor 310, a second operational amplifier 320, a third resistor 330 presenting a resistance R1, and a fourth resistor 340 presenting a resistance R4. The output 120 is coupled to an output of the second operational amplifier 320 and to an insulated gate terminal of the second transistor 310.

The first transistor 210 also includes a source terminal coupled to a first terminal of the first resistor 230, and a drain terminal coupled to a first terminal of the second resistor 240. A second terminal of the second resistor 240 is coupled to a point of the circuit where the voltage $V_c$ is maintained at an essentially constant value, for example, −5.25 V.

The first operational amplifier 220 is provided with a non-inverting input V+ coupled to a point of the circuit where the reference voltage $V_{ref}$ is maintained to a constant value, for example, −5 V. The first operational amplifier 220 is also provided with an inverting input V− coupled to the drain terminal of the first transistor 210, to the first terminal of the second resistor 240, and to an inverting input V− of the second operational amplifier 320.

The output of the operational amplifier 220 is coupled to a second terminal of the first resistor 230 and to a first terminal of the third resistor 330.

The first operational amplifier 220 is arranged to provide a variable tension to the source terminal of the first transistor 210, according to a comparison between the reference voltage $V_{ref}$ received on its non-inverting input V+ and the voltage $V_{R2}$ received on its inverting input V−. The first operational amplifier 220 is arranged to control the operating point (also known as Q-point or bias point) of the first transistor 210 so as that the first transistor 210 operates without saturation, distortion or other non-linear disturbances, for a wide range of values of the input voltage $V_{IN}$, for example, between 0.25 to 5.5 Volt. By performing as described, the first operational amplifier 220 remains at almost the same operating point, over a wide range of values of the input voltage $V_{IN}$, since the gate is not linearly controlled in relation with the current flowing between the source and the drain of the first operational amplifier 220, maintaining an essentially fixed operating point which allows for increased accuracy of the behavior of the first operational amplifier 220, by reducing non-linear behavior over a wide range of values for the input voltage $V_{IN}$. The error introduced by the interface unit in the output voltage $V_{OUT}$ comparatively to the input voltage $V_{IN}$ is drastically reduced, as illustrated for example in FIG. 6.

By contrast, in known solutions where a steady-state DC voltage or constant current is applied for biasing the source of the transistor, the input voltage may vary only on a much more limited range of values for the input voltage compared to exemplar embodiments disclosed herein, since saturation and/or distortion issues occur due to the fixed nature of the biasing current.

The second transistor 310 is provided with an insulated gate terminal coupled to the output of the second operational amplifier 320, a source terminal coupled to a second terminal of the third resistor 330, and a drain terminal coupled to a first terminal of the fourth resistor 240. A second terminal of the fourth resistor 340 is coupled to a point of the circuit where the voltage $V_C$ is maintained.

The second operational amplifier 320 is provided with a non-inverting input V+ coupled to the drain terminal of the second transistor 310 and to the first terminal of the fourth resistor 340. The second operational amplifier 320 is also provided with an inverting input V− coupled to the inverting input V− of the first operational amplifier 320, to the first terminal of the second resistor 240 and to the drain terminal of the first transistor 210.

The potential mirroring circuit 300 and the decoupling circuit 200 can share a balanced symmetrical design, in the sense that:
the resistance R1 of the first resistor 230 and the resistance R3 of the third resistor 330 are essentially identical; and,
the resistance R2 of the second resistor 240 and the resistance R4 of the fourth resistor are essentially identical; and,
the first transistor 210 and the second transistor 310 have essentially equivalent features and performances, and/or are of the same type.

In particular, the same type of electronic component may be used for the first resistor 230 and the third resistor R3. The same type of electronic component may be used for the first transistor 210 and the second transistor 310. The same type of electronic component may be used for the first operational amplifier 220 and the second operational amplifier 320. Since the potential mirroring circuit 300 and the decoupling circuit 200 are sharing a balanced symmetrical design, the cumulative influence on the interface unit 4 of the variations of the environmental parameters, such as the variation of temperatures, of the manufacturing tolerances for the electrical components, and of the electrical noises, can be greatly reduced, compared to circuits with a non-symmetrical design.

In an exemplary embodiment, the first transistor 210 and/or the second transistor 310 is/are a metal-oxide-semiconductor field-effect transistor (MOSFET), configured so as to adapt its conductivity $\sigma_{DEC}$ according to its gate terminal.

In an exemplary embodiment, the first transistor 210 and/or the second transistor 310 is/are an insulated gate field-effect transistor (IGFET). The first transistor 210 and/or the second transistor 310 are provided without an electrostatic-discharge protecting element at gate. Consequently, the interface unit may be implemented using variety of different types of transistors, thereby giving more flexibility during the manufacturing process in allowing finding second sources of supply and optimizing costs.

In another exemplary embodiment, the first transistor 210 and/or the second transistor 310 is/are a metal-insulator-semiconductor field-effect transistor (MISFET).

In another exemplary embodiment, the first transistor 210 and/or the second transistor 310 is/are is an insulated-gate bipolar transistor (IGBT).

Since the first transistor 210 and/or the second transistor 310 may be chosen notably amongst the aforementioned options, the interface unit can be implemented using a large variety of different types of transistors, thereby offering more flexibility during the manufacturing process in allowing finding second sources of supply and/or optimizing costs.

In an advantageous exemplary embodiment, the first operational amplifier 220 and the second operational amplifier 320 are embedded in one package of a single electronic component, and/or the first transistor 210 and the second transistor 310 are embedded in one package of a single electronic component. These features allow to further improve the reduction of the influence of the variations of the environmental parameters, of the manufacturing tolerances for the electrical components, and of the electrical noises. The footprint of the interface unit may also be further reduced, while the production cost may be lowered.

The first transistor 210 is arranged to generate a decoupled voltage $V_{R2}$ in the second resistor 240, according to the input voltage $V_{IN}$ received on the insulated gate terminal. More particularly, the decoupled voltage $V_{R2}$ in the second resistor 240 is proportional to the current flowing in the first resistor 230 through the source to the gate of the first transistor 240 into the second resistor 240. By coupling the first transistor 210 to the input 110 through the insulated gate terminal, current leakage through the input 110 can be drastically reduced. Consequently, the first transistor 210 behaves as an insulation barrier between the input 110 and the rest of the interface unit, and in particular the output 120, avoiding loading the input 110.

Since the inverted gate V− of the second operational amplifier 320 is coupled to the first terminal of second resistor 240, and the second terminal of the second resistor 240 is maintained at the voltage $V_C$, the output voltage $V_{OUT}$ delivered by the output terminal of the second operational amplifier 320 is controlling the gate of the second transistor 310 according to the voltage $V_C$. Consequently, the second transistor 310 behaves similarly to the first transistor 210. Being arranged so as to replicate the behavior of the first transistor 210, the second transistor 310 ensures symmetrical operations of the interface unit 4.

The second transistor 310 is arranged to generate a voltage $V_{R4}$ in the fourth resistor 340, according to the output voltage $V_{OUT}$ delivered by the output terminal of the second operational amplifier 320, received on the insulated gate terminal. Moreover, the output 130 is also coupled to the insulated gate terminal of the second operational amplifier 320. More particularly, the voltage $V_{R4}$ in the fourth resistor 240 is proportional to the current flowing in the third resistor 330 through the source to the gate of the second transistor 310 into the fourth resistor 340. Hence, by coupling the output terminal of the second operational amplifier 320 to the output 120, the interface unit 4 is capable of producing robustly the output voltage $V_{OUT}$.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

REFERENCE SIGNS LIST 1 electrochemical measuring probe
2 signal leads
3 evaluating device
4 interface unit
6 measurement material
8 container
81 holding vessel
500 processing device
11 inner tube
12 outer tube
13 outer buffer
14 inner buffer
15 reference electrode
16 glass electrode
17 temperature measuring sensor
18 auxiliary electrode
111 thin-walled glass hemisphere or glass membrane
121 diaphragm
19 signal wire
110 interface unit input
120 interface unit output
200 decoupling circuit
210 first transistor
220 first operational amplifier
230 first resistor
240 second resistor
300 potential mirroring circuit
310 second transistor
320 second operational amplifier
330 third resistor
340 fourth resistor

The invention claimed is:

1. An interface unit comprising:
   an input configured and adapted to receive an input current having an input voltage ($V_{IN}$), from an electrochemical measuring probe for use in contact with a process material, the electrochemical measuring probe having an electrode (EL) provided with a sensing element arranged so as to generate a sensor voltage ($V_{SENSOR}$) as an electrode voltage related to at least one property of the process material when the electrode is in contact with the process material;
   an output configured and adapted to be coupled to an input of an evaluating device, the interface unit being configured to deliver, on the output, an output current having an output voltage ($V_{OUT}$) essentially equal to the input voltage ($V_{IN}$);
   a first transistor provided with a first insulated gate terminal coupled to the input, a first source terminal coupled to a first terminal of a first resistor, and a first drain terminal coupled to a first terminal of a second resistor, a second terminal of the second resistor being coupled to a point where a constant voltage ($V_C$) is maintained to a constant value, the first transistor being configured and arranged to generate in the second resistor a second resistor voltage ($V_{R2}$), according to the input voltage ($V_{IN}$);
   a first operational amplifier provided with a first non-inverting input coupled to a circuit point where a reference voltage ($V_{ref}$) is maintained to a constant value, with a first inverting input coupled to a first drain terminal of the first transistor, and with a first output coupled to a second terminal of the first resistor;
   a second transistor provided with a second source terminal coupled to a second terminal of a third resistor, and a second drain terminal coupled to a first terminal of a fourth resistor, a first terminal of the third resistor being coupled to the second terminal of the first resistor, a second terminal of the fourth resistor being coupled to a point where the constant voltage ($V_C$) is maintained; and
   a second operational amplifier provided with a second non-inverting input coupled to the second drain terminal of the second transistor, and with a second inverting input coupled to the first inverting input of the first operational amplifier, and with a second output coupled a second insulated gate terminal of the second transistor and to the output of the interface unit;
   wherein the first operational amplifier is configured and arranged to provide a variable tension to the first source terminal of the first transistor in accordance with a comparison between the reference voltage ($V_{ref}$) and the second resistor voltage ($V_{R2}$), in order to control an operating point of the first transistor.

2. The interface unit according to claim 1, wherein the first resistor has a resistance essentially identical to a resistance of the third resistor, and wherein the second resistor has a resistance essentially identical to a resistance of the fourth resistor.

3. The interface unit according to claim 1, wherein the first transistor and the second transistor are of a same transistor type.

4. The interface unit according to claim 1, wherein the first operational amplifier and the second operational amplifier are embedded in one package of a single electronic component.

5. The interface unit according to claim 1, wherein the first transistor and the second transistor are embedded in one package of a single electronic component.

6. The interface unit according to claim 1, wherein at least one of the first transistor and/or the second transistor is/are an insulated gate field-effect transistor, or a metal-oxide-semiconductor field-effect transistor, or a metal-insulator-semiconductor field-effect transistor, or an insulated-gate bipolar transistor.

7. A measuring system comprising, in combination:
   an interface unit according to claim 1;
   an electrochemical measuring probe configured for use in contact with a process material, the probe including an electrode (EL) provided with a sensing element configured and arranged so as to generate a sensor voltage ($V_{SENSOR}$) as an electrode voltage related to at least one property of the process material when the electrode is in contact with the process material, the electrochemical measuring probe being configured and adapted to deliver the sensor voltage ($V_{SENSOR}$) to the input of the interface unit; and
   an evaluating device provided with an input configured and adapted to be coupled to the output of the interface unit, for receiving the output voltage ($V_{OUT}$), for converting the output voltage into measurements.

8. The measuring system according to claim 7, wherein the sensing element of the electrode comprises:
   an active layer behaving as a voltage source, the electrode voltage differing from zero even when the electrode is not in contact with the process material.

9. The measuring system according to claim 7, wherein the measuring probe is selected from the group consisting of: a pH measuring probe, an oxygen measuring probe, a $CO_2$ measuring probe, and an ozone measuring probe.

10. The measuring system according to claim 7, wherein the sensing element of the electrode comprises:
a lithium phosphorus oxynitride layer.

11. The interface unit according to claim 2, wherein the first transistor and the second transistor are of a same transistor type.

12. The interface unit according to claim 11, wherein the first operational amplifier and the second operational amplifier are embedded in one package of a single electronic component.

13. The interface unit according to claim 12, wherein the first transistor and the second transistor are embedded in one package of a single electronic component.

14. The interface unit according to claim 13, wherein at least one of the first transistor and/or the second transistor is/are an insulated gate field-effect transistor, or a metal-oxide-semiconductor field-effect transistor, or a metal-insulator-semiconductor field-effect transistor, or an insulated-gate bipolar transistor.

15. A measuring system comprising, in combination:
an interface unit according to claim 14;
an electrochemical measuring probe configured for use in contact with a process material, the probe including an electrode (EL) provided with a sensing element configured and arranged so as to generate a sensor voltage ($V_{SENSOR}$) as an electrode voltage related to at least one property of the process material when the electrode is in contact with the process material, the electrochemical measuring probe being configured and adapted to deliver the sensor voltage ($V_{SENSOR}$) to the input of the interface unit; and
an evaluating device provided with an input configured and adapted to be coupled to the output of the interface unit, for receiving the output voltage ($V_{OUT}$), for converting the output voltage into measurements.

16. The measuring system according to claim 15, wherein the sensing element of the electrode comprises:
an active layer behaving as a voltage source, the electrode voltage differing from zero even when the electrode is not in contact with the process material.

17. The measuring system according to claim 16, wherein the measuring probe is selected from the group consisting of: a pH measuring probe, an oxygen measuring probe, a $CO_2$ measuring probe, and an ozone measuring probe.

18. The measuring system according to claim 17, wherein the sensing element of the electrode comprises:
a lithium phosphorus oxynitride layer.

* * * * *

UNITED STATES PATENT AND TRADEMARK OFFICE
CERTIFICATE OF CORRECTION

| | |
|---|---|
| PATENT NO. | : 11,549,966 B2 |
| APPLICATION NO. | : 17/011430 |
| DATED | : January 10, 2023 |
| INVENTOR(S) | : Daniel Jungo |

It is certified that error appears in the above-identified patent and that said Letters Patent is hereby corrected as shown below:

In the Specification

Column 1, Line 8 reads "Sep. 10, 2020" should read "Sep. 10, 2019".

Column 2, Line 5 reads "Interface—Sparky's Widgets" should read "Interface-Sparky's Widgets".

Column 2, Line 50 reads "0.25and" should read "0.25 and".

Column 9, Line 41 reads "impedance In" should read "impedance Zin".

Signed and Sealed this
Second Day of May, 2023

Katherine Kelly Vidal
*Director of the United States Patent and Trademark Office*